(12) United States Patent
Dukart et al.

(10) Patent No.: US 7,781,446 B2
(45) Date of Patent: *Aug. 24, 2010

(54) USE OF CCI-779 AS AN ANTINEOPLASTIC AGENT

(75) Inventors: Gary Dukart, Ambler, PA (US); James J. Gibbons, Jr., Westwood, NJ (US); Lisa Anne Speicher, Havertown, PA (US); Philip Frost, Morris Township, NJ (US); Carolyn Mary Discafani-Marro, Cortlandt Manor, NY (US)

(73) Assignee: Wyeth LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/701,109

(22) Filed: Feb. 1, 2007

(65) Prior Publication Data

US 2007/0142425 A1    Jun. 21, 2007

Related U.S. Application Data

(63) Continuation of application No. 10/374,644, filed on Feb. 26, 2003, now Pat. No. 7,189,735, which is a continuation of application No. 10/010,584, filed on Nov. 13, 2001, now abandoned.

(60) Provisional application No. 60/249,077, filed on Nov. 15, 2000.

(51) Int. Cl.
    *A61K 31/44* (2006.01)

(52) U.S. Cl. .................. 514/291; 514/183; 514/311; 514/312; 514/313

(58) Field of Classification Search ................ 514/291, 514/183, 311, 312, 313
    See application file for complete search history.

(56) References Cited

U.S. PATENT DOCUMENTS

| | | | |
|---|---|---|---|
| 3,929,992 A | 12/1975 | Sehgal et al. | |
| 3,993,749 A | 11/1976 | Sehgal et al. | |
| 4,401,653 A | 8/1983 | Eng | |
| 4,885,171 A | 12/1989 | Surendra et al. | |
| 5,078,999 A | 1/1992 | Warner et al. | |
| 5,080,899 A | 1/1992 | Sturm et al. | |
| 5,100,899 A | 3/1992 | Calne et al. | |
| 5,206,018 A | 4/1993 | Sehgal et al. | |
| 5,286,730 A | 2/1994 | Caufield et al. | |
| 5,286,731 A | 2/1994 | Caufield et al. | |
| 5,288,711 A | 2/1994 | Mitchell et al. | |
| 5,321,009 A | 6/1994 | Baeder et al. | |
| 5,362,718 A * | 11/1994 | Skotnicki et al. | 514/63 |
| 5,387,589 A | 2/1995 | Kulkarni et al. | |
| 5,496,832 A | 3/1996 | Armstrong et al. | |
| 5,516,781 A | 5/1996 | Morris et al. | |
| 5,561,138 A | 10/1996 | Armstrong et al. | |
| 5,728,710 A | 3/1998 | Luengo | |
| 6,617,333 B2 | 9/2003 | Rabindran et al. | |

| | | | |
|---|---|---|---|
| 2002/0183239 A1 | 12/2002 | Gibbons | |
| 2002/0183240 A1 | 12/2002 | Gibbons | |

FOREIGN PATENT DOCUMENTS

| | | |
|---|---|---|
| EP | 0 525 960 A1 | 2/1993 |
| WO | WO 02/13802 A2 | 2/2002 |

OTHER PUBLICATIONS

B. Geoerger, et al., Cancer Research, Feb. 15, 2001, vol. 61, No. 4, pp. 1527-1532.
G. Schwartsmann, et al., Annals of Oncology, Oct. 13, 2000, vol. 11, No. 3, pp. 235-243.
S.N. Sehgal, et al., J. Antibiot., 1975, 727, 28.
C.V. Vezina, et al., J. Antibiot., 1975, 721, 28.
H.A. Baker, et al., J. Antibiot., 1978, 539, 31.
Faseb, 1989, 3411, 3.
Faseb, 1989, 5256, 3.
R.Y. Calne, et al., Lancet, 1978, 1183.
R. Martel, et al., Can. J. Physiol. Pharmacol., 1977, 48, 55.
J. Alexandre, et al., Bull. Cancer, 1999, 808, 86.
A. Perren, et al., Am. J. Pathology, 1999, 1253, 155.
J.E. Dancey, et al., ASCO Educational Book, Spring 2000, 68.
M. Hidalgo, et al., Oncogene, 2000, 6680, 19.
E.A. Sausville, et al., ASCO Educational Book, Fall, 1998, 112.
J. Alexandre, et al., CCI-779, a new rapamycin analog, has antitumor activity at doses inducing only mild cutaneous effects and mucostitis; early results of an ongoing phase 1 study, Proceedings of the 10th NCI/EORTC/AACR Symposium, 1999 (poster presentation).
J.J. Gibbons, et al., Proceedings of the American Association for Cancer Research, 1999, 301a, 40.
B. Geoerger, et al., Proceedings of the American Association for Cancer Research, 1999, 603a, 40.
J, Alexandre, et al., Proceedings of the American Association for Cancer Research, 2000, 613, 41.
M. Hidalgo, et al., Proceedings of the 11th NCI/EORTC/AACR Symposium, 2000, 4548s, 6 (Supp.).
M. Hidalgo, et al., Annals of Oncology, 2000, 133a, 11(4).
E. Raymond, et al., Proceedings of the 11th NCI/EORTC/AACR Symposium, 2000, Ab, 414.
E. Raymond, et al., Proceedings of the ASCO, 2000, 187a, 19.
M. Hidalgo, et al., Phase 1 and Pharmacological Studies with the Rapamycin Analog CCI-779 Administered as a 30 Minute Infusion, NCI-CTEP, Drug Development Meeting, Oct. 1999.
M. Abou-Gharbia, Medicinal Chemistry Approaches for Optimization of Early Leads in Drug Candidates: The Discovery of Calicheamicin, Rapamycin and EAA-090, International Conference on Pure and Applied Heterocyclic Chemistry, Mar. 2000.

(Continued)

*Primary Examiner*—James D Anderson
(74) *Attorney, Agent, or Firm*—Howson & Howson LLP; David A. Rubin

(57) ABSTRACT

This invention provides the use of CCI-779 in the treatment of neoplasms.

2 Claims, No Drawings

OTHER PUBLICATIONS

R. Langreth, et al., The Wall Street Journal, Nov. 17, 1999, vol. 234.
Carter, et al., Chemotherapy of Cancer, second edition, 1981, pp. 362-365, John Wiley & Sons, N.Y., N.Y.
Alberts, New Perspectives on an Old Friend: optimizing carboplatin for the treatment of solid tumors, Oncologist, 1998, 3(1): 15-34, Abstract.
Dorland'S Illustrated Medical Dictionary, 24th Edition, p. 987, 1965.
P. Robins, Poster Highlights 1, IDrugs, 1999, vol. 2, No. 6, Paragraph, CCI-779, XP-001083882.
Yu, et al., "mTOR, a novel target in breast cancer: the effect of CCI-779, an mTOR inhibitor, in preclinical models of breast cancer", Endocr. Relat. Cancer, 8(3):249-258 (Sep. 2001).
Raymond, et al., "CCI-779, a rapamycin analog with antitumor activity: a phase I study utilizing a weekly schedule", Proc. Am. Soc. Clin. Oncol. 19(abstr. 728) (Annual Meeting, May 20-23, 2000).
M. Hidalgo, et al., CCI-779, a Rapamycin Analog and Multifaceted Inhibitor of Signal Transduction: a Phase I Study, Proceedings of the American Society of Clinical Oncology 2000 Annual Meeting, May 20-23, 2000.
Schmelzle, et al., "TOR, a central controller of cell growth," Cell, vol. 103, No. 2, (Oct. 13, 2000) pp. 253-262.
Friedrich, "Von Hippel-Lindau Syndrome, A Pleomorphic Condition", Cancer, 86(S11):2478-2482 (Jun. 1998)(presented at the American Cancer Society Second National Conference on Cancer Genetics, San Francisco, CA, Jun. 26-28, 1998; published in journal Dec. 1, 1999).
Hidalgo, "The rapamycin-sensitive signal transduction pathway as a target for cancer therapy", Oncogene, 19:6680-6686 (Dec. 27, 2000).
Maxwell, "The tumor suppressor protein VHL targets hypoxia-inducible factors for oxygen-dependent proteolysis", Nature, 399:271-275 (May 20, 1999).
Zhong, "Modulation of Hypoxia-inducible Factor $1\alpha$ Expression by the Epidermal Growth Factor/Phosphatidylinositiol 3-Kinase/PTEN/AKT/FRAP Pathway in Human Prostate Cancer Cells: Implications for Tumor Angiogenesis and Therapeutics", Cancer Research, 60:1541-1545 (Mar. 15, 2000).
English-language translation of a Notice of Reexamination issued Jul. 27, 2009 in counterpart Chinese Patent Application No. 01818926.1.
English-language translation of a Final Rejection mailed May 19, 2009 in counterpart Japanese Patent Application No. 2002-542375.
English translation of an Examination Report dated Oct. 18, 2009 issued in counterpart Chilean Patent Application No. 02739-2001.

* cited by examiner

USE OF CCI-779 AS AN ANTINEOPLASTIC AGENT

CROSS-REFERENCE TO RELATED APPLICATIONS

This application is a continuation of U.S. patent application Ser. No. 10/374,644, filed Feb. 26, 2003 (now U.S. Pat. No. 7,189,735, issued Mar. 13, 2007), which is a continuation of U.S. patent application Ser. No. 10/010,584, filed Nov. 13, 2001, which claims the benefit under 35 USC 119(e) of prior U.S. Provisional Patent Application No. 60/249,077, filed Nov. 15, 2000.

BACKGROUND OF THE INVENTION

This invention relates to the use of rapamycin 42-ester with 3-hydroxy-2-(hydroxymethyl)-2-methylpropionic acid (CCI-779) as an antineoplastic agent. Rapamycin is a macrocyclic triene antibiotic produced by *Streptomyces hvqroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749]. Additionally, rapamycin alone (U.S. Pat. No. 4,885,171) or in combination with picibanil (U.S. Pat. No. 4,401,653) has been shown to have antitumor activity.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R.Y. Calne et al., Lancet 1183 (1978); and U.S. Pat. No. 5,100,899]. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

Rapamycin is also useful in preventing or treating systemic lupus erythematosus [U.S. Pat. No. 5,078,999], pulmonary inflammation [U.S. Pat. No. 5,080,899], insulin dependent diabetes mellitus [U.S. Pat. No. 5,321,009], skin disorders, such as psoriasis [U.S. Pat. No. 5,286,730], bowel disorders [U.S. Pat. No. 5,286,731], smooth muscle cell proliferation and intimal thickening following vascular injury [U.S. Pat. Nos. 5,288,711 and 5,516,781], adult T-cell leukemia/lymphoma [European Patent Application 525,960 A1], ocular inflammation [U.S. Pat. No. 5,387,589], malignant carcinomas [U.S. Pat. No. 5,206,018], cardiac inflammatory disease [U.S. Pat. No. 5,496,832], and anemia [U.S. Pat. No. 5,561,138].

The preparation and use of hydroxyesters of rapamycin, including CCI-779, are disclosed in U.S. Pat. No. 5,362,718.

DETAILED DESCRIPTION OF THE INVENTION

This invention provides, the use of CCI-779 as an antineoplastic agent, and particularly for neoplasms which are refractory to standard therapy, or for whom standard therapy is not appropriate. In particular CCI-779 is useful in the treatment of renal cancer, soft tissue cancer, breast cancer, neuroendocrine tumor of the lung, cervical cancer, uterine cancer, head and neck cancer, glioblastoma, non-small lung cell cancer, prostate cancer, pancreatic cancer, lymphoma, melanoma, small cell lung cancer, ovarian cancer, endometrial cancer, and colon cancer.

As used in accordance with this invention, the term "treatment" means treating a mammal having a neoplastic disease by providing said mammal an effective amount of CCI-779 with the purpose of inhibiting growth of the neoplasm in such mammal, eradication of the neoplasm, or palliation of the neoplasm.

As used in accordance with this invention, the term "providing," with respect to providing CCI-779, means either directly administering CCI-779, or administering a prodrug, derivative, or analog which will form an effective amount of CCI-779 within the body.

As used in accordance with this invention, the term "refractory neoplasm" refers to neoplasms in patients which typically had progressed following treatment with standard chemotherapy that was appropriate for that given neoplasm.

The preparation of CCI-779 is described in U.S. Pat. No. 5,362,718, which is hereby incorporated by reference.

The antineoplastic activity of CCI-779 was confirmed in a preclinical in vitro and in vivo standard pharmacological test procedure which measured the ability of CCI-779 to treat human renal cell cancer (a rapidly progressive disease with very limited treatment options), as well as in two Phase 1 human clinical trials. The procedures used and results obtained are briefly described below.

Preclinical Test Procedures

In vitro test procedure: Renal tumor lines HTB-44 and CRL-1161 were obtained from the American Tissue Culture Collection (ATCC), Bethesda, Md. SN12-C line was obtained from Dr. J. Fidler, M. D. Anderson Hospital, Houston, Tex. Cells were plated in MEM (Gibco) supplemented with 2 mM glutamine, 1 mM sodium pyruvate, 5 ml penicillin-streptomycin solution, 1 mM non-essential amino acid solution, 10% fetal bovine solution. Cells ($5 \times 10^3$) were plated in 96 well plates with a final volume of 200 ml and incubated for 24 hours at 37° C. Log dilutions of CCI-779 beginning at 100 µg/ml were then added to the cultures for 48 hours. Over the last 5 hours, cells were pulsed with 1 µci $^3$H-thymidine (New England Nuclear, 6.7 ci/m Mol). Cells were then harvested and the degree of thymidine uptake determined by liquid scintillation spectrometry. The $IC_{50}$ was determined as the concentration that produced 50% of the maximum uptake of thymidine in control untreated cells.

In vivo test procedure: Female Balb/c nu/nu mice were obtained from Charles River Labs, Wilmington, Del., at 6-8 weeks of age. Mice (n=10/group) were injected sc with $5 \times 10^6$ cells resuspended in a 50% solution of Matrigel (BD Biosciences) and tumors allowed to develop. When tumor size reached 100 mg, mice were treated orally with CCI-779 at 25 mg/kg. CCI-779 was dosed for 5 consecutive days with repeated 14 day cycles throughout the duration of the experiment. The formulation used for CCI-779 was a 50% ethanol, 49% phosal, 1% tween 80 vehicle for resuspending CCI-779, where the stock was resuspended into a 1:10 dilution of the vehicle prior to dosing. Tumor growth was evaluated using a vernier caliper and volume (l×w×h) was converted to mass using the formula: $l \times w^2/2$.

Results:

Human renal cell tumors were cultured in vitro in the presence or absence of CCI-779 for 3 days and the effect on growth determined by $^3$H-thymidine incorporation of control versus treated cells. Table 1 shows that $IC_{50}$ (50% growth inhibitory concentration) for all 3 lines tested was in the low nM range.

TABLE 1

The effect of CCI-779 on the growth of human renal tumor cells in vitro

| Renal Tumor Line | CCI-779 IC$_{50}$ (nM) |
| --- | --- |
| HTB-44 | 5.0 |
| CRL-1161 | 2.0 |
| SN12-C | 5.5 |

The effect of CCI-779 in two human renal lines (HTB-44 and CRL-1161) was evaluated in vivo by engrafting tumor cells on the flanks of nude mice. Once tumors were established at a size of about 100 mg, mice were treated with CCI-779 or a vehicle control. Treatment with CCI-779 at 25 mg/kg resulted in significant inhibition of tumor cell growth in the mice (Table 2).

TABLE 2

Effect of CCI-779 on the growth of human renal tumor cells in nude mouse xenografts

| Cell Line | Drug Treatment | Tumor Mass (mg) Days | | | | | |
| --- | --- | --- | --- | --- | --- | --- | --- |
| | | 0 | 7 | 21 | 35 | 49 | 55 |
| HTB-44 | Control | 288 ± 21 | 219 ± 18 | 616 ± 55 | 1095 ± 44 | 2033 ± 247 | 2412 ± 342 |
| | CCI | 290 ± 15 | 156 ± 13* | 252 ± 48* | 453 ± 85* | 980 ± 155* | 1050 ± 183* |
| | % T/C | 101 | 71 | 41 | 41 | 48 | 44 |
| CRL-1161 | Control | 273 ± 18 | 355 ± 36 | 413 ± 60 | 480 ± 127 | 546 ± 170 | 507 ± 156 |
| | CCI | 272 ± 14 | 219 ± 16* | 226 ± 17* | 200 ± 21* | 229 ± 28* | 268 ± 30 |
| | % T/C | 100 | 62 | 60 | 42 | 42 | 53 |

*p value - <.05
% T/C - Treated/Control × 100

Clinical Trial:

Two single agent (CCI-779) Phase I clinical trials have been conducted. In the first study, CCI-779 was administered as a 30 minute i.v. infusion daily for 5 days, every two to three weeks. In the second study, CCI-779 was administered as a 30 minute i.v. infusion, once weekly. Both trials were open label, ascending dose, single-arm, multicenter studies. Patients were allowed to continue treatment as long as the CCI-779 was tolerated and there was no evidence of obvious disease progression. The following eligibility criteria were used:

Inclusion Criteria

1. Patients with a histologic diagnosis of advanced cancer (solid tumors and, in the first study, lymphomas) who are refractory to standard therapy or for whom standard therapy is not appropriate.
2. Measurable or evaluable disease.
3. At least 3 weeks since prior chemotherapy and/or radiation therapy (6 weeks since nitrosoureas or mitomycin C).
4. At least 4 weeks since any other investigational agent.
5. Age at least 18 years old.
6. Adequate bone marrow, renal, and hepatic function.
7. Serum cholesterol<350 mg/dL and triglycerides 1300 mg/dL.
8. ECOG performance status 0-2.
9. Life expectancy of at least 3 months.
10. Signed, dated, witnessed written informed consent.

A total of 63 patients and 24 patients were enrolled in first and second studies, respectively. Dose levels ranged from 0.75-24 mg/m$^2$ and 7.5-220 mg/m$^2$, with the daily×5 every 2 weeks and weekly schedules, respectively.

The following summarizes the results that were obtained:

In patients having renal cancer on the weekly schedule, 1 partial response ($\geq$50% reduction in tumor size) and 2 minor responses ($\geq$25% but<50% reduction in tumor size) were observed. In renal cancer patients on the daily×5 schedule, 1 minor response, 1 unconfirmed minor response, and 1 stable disease (<25% increase to <25% reduction in tumor size) lasting approximately 5 months were observed. In patients having soft tissue sarcoma on the daily×5 dosage schedule, 1 possible partial response, 2 minor responses, and 1 stable disease lasting approximately 5½ months were observed. In patients with breast cancer on the weekly dosage schedule, one partial response was observed. In patients with neuroendocrine tumor of the lung on the weekly dosage schedule, one partial response was observed. In patients having cervical cancer on the daily×5 dosage schedule, one minor response was observed. In patients having uterine cancer receiving the daily×5 dosage schedule, one unconfirmed minor response was observed. In patients having head and neck cancer receiving the daily×5 dosage schedule, 1 stable disease for approximately 8½ months was observed. In patients having non-small cell lung cancer receiving the daily×5 dosage schedule, one partial response was observed. These results are particularly surprising, considering that the patients in these studies had advanced cancers that were generally refractory to standard treatment, and also considering that these were Phase I clinical trials, in which efficacy is often limited, as the primary objective of a Phase I trial is to determine the safety and tolerability of the drug being evaluated.

Based on the results of the preclinical and clinical test procedures, CCI-779 is useful in treating neoplasms, in particular, refractory neoplasms. More particularly, CCI-779 is useful in the treatment of renal carcinoma, soft tissue carcinoma, breast cancer, neuroendocrine tumor of the lung, cervical cancer, uterine cancer, head and neck cancer, glioblastoma, non-small cell lung cancer, prostate cancer, pancreatic cancer, lymphoma, melanoma, small cell lung cancer, ovarian cancer, endometrial cancer, and colon cancer.

As typical with chemotherapy, dosage regimens are closely monitored by the treating physician, based in numerous factors including the severity of the disease, response to the disease, any treatment related toxicities, age, and health of the patient. Based on the results obtained with CCI-779, it is projected that initial i.v. infusion dosages will be between about 0.1 and 100 mg/m$^2$ when administered on a daily dosage regimen, and between about 1 and 1000 mg/m$^2$ when administered on a weekly dosage regimen. Other dosage regimens and variations are foreseeable, and will be determined through physician guidance. It is preferred that CCI-779 is administered by i.v. infusion or orally, preferably in the form of tablets or capsules. Other routes of administration are also feasible, such as via implants, parenterally (besides i.v., such as intraperitoneal and subcutaneous injections), rectally, intranasally, vaginally, and transdermally.

Dosage regimens are expected to vary according to the route of administration. For example, dosages for oral administration are often up to tenfold greater than for i.v. administration. It is anticipated that CCI-779 may be administered as the sole active chemotherapeutic agent, or may be part of a chemotherapeutic regimen containing more than one antineoplastic agent. The use of concomitant chemotherapeutic agents often allows for dosage reduction of each particular agent, thereby increasing the safety margin of the particular agents.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert. fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The invention claimed is:

1. A method of treating a refractory neoplasm in a mammal in need thereof, which comprises providing to said mammal a therapeutically effective amount of CCI-779, wherein said mammal has been previously treated with standard chemotherapy and wherein said refractory neoplasm has progressed following treatment with said standard chemotherapy, wherein said refractory neoplasm is renal cancer.

2. A method of reducing the size of a refractory human renal cell tumor in a human patient, which comprises providing to said human patient a therapeutically effective amount of CCI-779, wherein said human patient has been previously treated with standard chemotherapy and wherein said refractory human renal cell tumor has progressed following treatment with said standard chemotherapy.

* * * * *